United States Patent
Ali et al.

(10) Patent No.: US 8,367,711 B2
(45) Date of Patent: Feb. 5, 2013

(54) ANGIOTENSIN II RECEPTOR ANTAGONISTS

(75) Inventors: Amjad Ali, Freehold, NJ (US); Michael Man-Chu Lo, Edison, NJ (US); Christopher Franklin, Quincy, MA (US); Iyassu K. Sebhat, Jersey City, NJ (US); Nicoletta Almirante, Milan (IT); Silvia Stefanini, San Donato Milanese (IT); Stefano Biondi, Pero (IT); Ennio Ongini, Segrate (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/483,213

(22) Filed: May 30, 2012

(65) Prior Publication Data

US 2012/0238608 A1    Sep. 20, 2012

Related U.S. Application Data

(62) Division of application No. 12/992,330, filed as application No. PCT/US2009/042951 on May 6, 2009, now Pat. No. 8,207,208.

(60) Provisional application No. 61/127,807, filed on May 15, 2008.

(51) Int. Cl.
*A61K 31/41* (2006.01)
*A61K 31/405* (2006.01)
*C07D 209/00* (2006.01)
*C07D 257/04* (2006.01)

(52) U.S. Cl. ........ 514/381; 514/415; 514/509; 548/250; 548/452; 558/482

(58) Field of Classification Search ............. 514/381, 514/415, 509; 548/250, 452; 558/482
See application file for complete search history.

(56) References Cited

U.S. PATENT DOCUMENTS

| | | | |
|---|---|---|---|
| 6,391,895 B1 | 5/2002 | Towart et al. | |
| 7,858,651 B2 * | 12/2010 | Guo et al. | 514/381 |
| 2007/0032533 A1 | 2/2007 | Garvey et al. | |

* cited by examiner

*Primary Examiner* — Susannah Chung
(74) *Attorney, Agent, or Firm* — Richard S. Parr; Catherine D. Fitch

(57) ABSTRACT

A compound having the structure wherein R is, for example, Y is selected from the group consisting of 1) R5, 2) —C(R1R2) (C(R3R4))0-1Y1R5, and 3) —C(R1R2)—O—Y1R5; R1, R2, R3 and R4 are independently selected from the group consisting of hydrogen and C1-4 alkyl; R5 is; Y1 is selected from the group consisting of C(O)—O— and P(O)(OR6)—O—; and R6 is hydrogen or CH3, or a pharmaceutically acceptable salt thereof, and methods of using the compounds for treating hypertension.

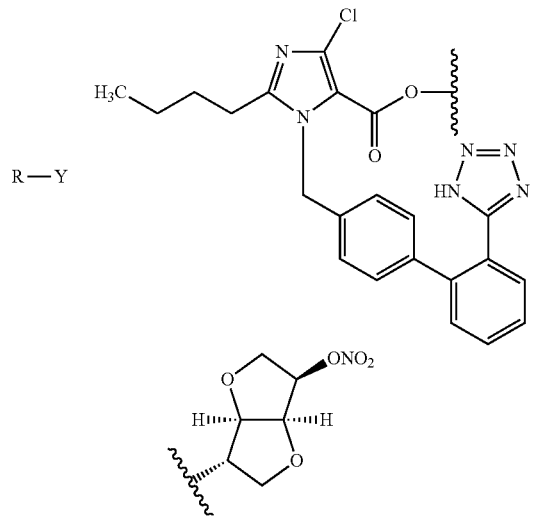

11 Claims, No Drawings

ANGIOTENSIN II RECEPTOR ANTAGONISTS

CROSS REFERENCE TO RELATED APPLICATIONS

This application is a divisional of U.S. Application No. 12/992,300 which was filed on Nov. 12, 2010 as a U.S. National Phase application under 35 USC Section 371 of PCT Application No. PCT/US2009/042951, filed May 6, 2009, which claims priority under 35 USC Section 119(e) from U.S. Application No. 61/127,807, filed May 15, 2008.

BACKGROUND OF THE INVENTION

U.S. Pat. No. 5,138,069 generically and specifically describes 2-butyl-4-chloro-1-[p-(o-1H-tetrazol-5-ylphenyl)-benzyl]imidazole-5-methanol potassium salt and 2-butyl-4-chloro-1-[(2'-1H-tetrazol-5-yl)biphenyl-4-yl)methyl]imidazole-5-carboxylic acid. Columns 261-263 of U.S. Pat. No. 5,136,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

WO2005011646 describes angiotensin II receptor blocker nitroderivatives, pharmaceutical compositions containing them and their use for the treatment of cardiovascular, renal and chronic liver diseases, inflammatory processes and metabolic syndromes. The publication describes a variety of angiotensin receptor blocker compounds each of which are covalently linked in a variety of ways to a nitric oxide group. Specific examples include angiotensin receptor blockers with one covalently-linked nitric oxide group, and angiotensin receptor blockers with two independently-covalently-linked nitric oxide groups. WO2005023182 describes nitrosated and nitrosylated cardiovascular compounds, and compositions comprising at least one nitrosated and nitrosylated cardiovascular compound and optionally at least one nitric oxide donor. The cardiovascular compound which is nitrosated or nitrosylated may be an aldosterone antagonist, an angiotensin II receptor antagonist, a calcium channel blocker, an endothelin antagonist, a hydralazine compound, a neutral endopeptidase inhibitor or a renin inhibitor. The nitric oxide donor may be selected from S-nitrosothiols, nitrites, nitrates, N-oxo-N-nitrosamines, fiiroxans, and sydnonimines.

WO2005070868 describes combination therapy for treating cyclooxygenase-2 mediated diseases or conditions at risk of thrombotic cardiovascular events which involves administering selected cyclooxygenase-2 inhibitor in combination with a nitric oxide donating compound such as 5,6-bis(nitrooxy)hexyl acetate, 6-hydroxyhexane-1,2-diyl dinitrate, 5-hydroxypentane-1,2-diyl dinitrate, (5R) -5,6-bis(nitrooxy) hexyl 4-nitrobenzoate, (5S)-5,6-bis(nitrooxy)hexyl 4-nitrobenzoate, (2R)-6-hydroxyhexane-1,2-diyl dinitrate, (2S)-6-hydroxyhexane-1,2-diyl dinitrate, (2S)-propane-1,2-diyl dinitrate, and (2R)-propane-1,2-diyl dinitrate.

SUMMARY OF THE INVENTION

The present invention includes angiotensin II receptor antagonist isosorbide mononitrate or its isomeric compounds such as isomannide mononitrate and isoidide mononitrate, and derivatives thereof, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin H receptor antagonist of the invention to a patient having one or more of these conditions.

DETAILED DESCRIPTION OF THE INVENTION AND PREFERRED EMBODIMENTS

Compounds of the invention are angiotensin H receptor antagonist (nitrooxy) derivatives having the general formula:

wherein R is selected from the group consisting of

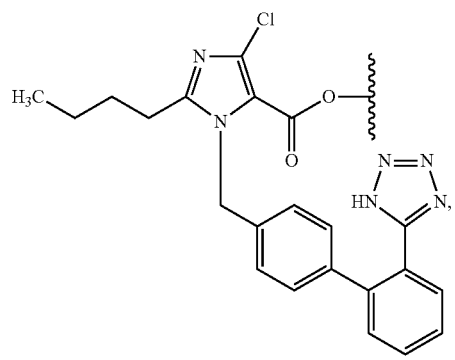

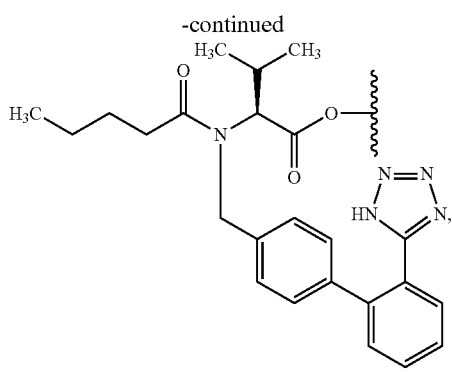
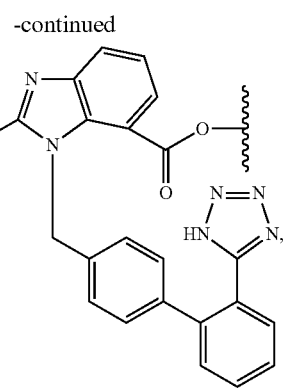
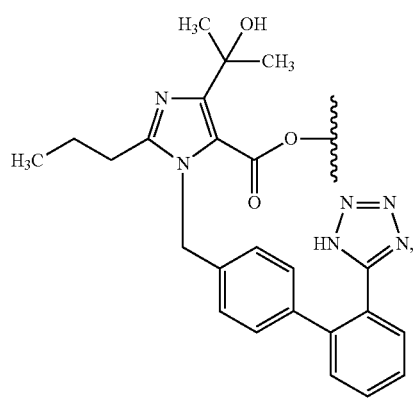
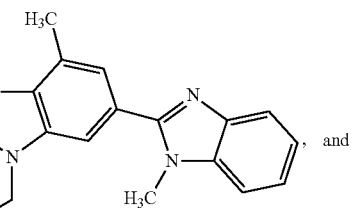
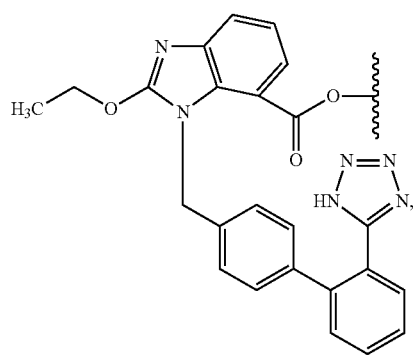
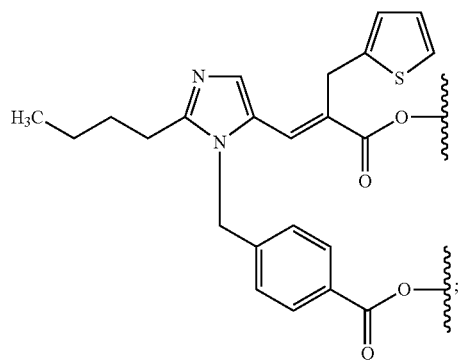
, and
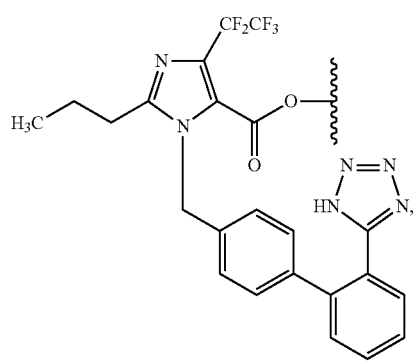
Y is selected from the group consisting of
1) R5,
2) —C(R¹R²)(C(R³R⁴))₀₋₁Y¹R⁵, and
3) —C(R¹R²)—O—Y¹R⁵,
or

is

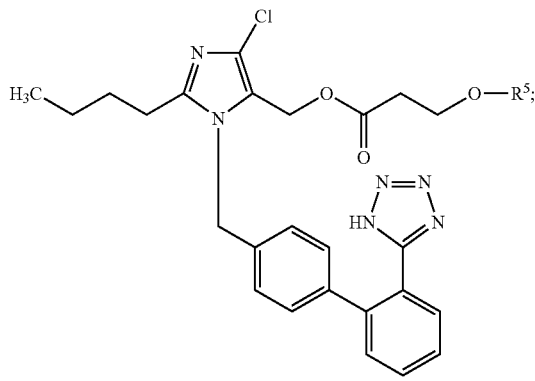

R[1], R[2], R[3] and R[4] are independently selected from the group consisting of hydrogen and $C_{1-4}$ alkyl; and R[5] is selected from the group consisting of

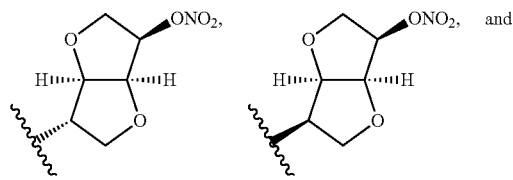

$Y^1$ is selected from the group consisting of —C(O)—O— and —P(O)(OR[6])—O—; and R6 is hydrogen or $CH_3$, or a pharmaceutically acceptable salt thereof.

In one embodiment of the invention, R[1], R[2], R[3] and R[4] are independently selected from the group consisting of hydrogen and $CH_3$.

In another embodiment of the invention, $Y^1$ is selected from the group consisting of —C(O)—O—, —P(O)(OH)—O—, and —P(O)(OCH_3)—O—.

In another embodiment of the invention, Y is selected from the group consisting of —C((CH_3)(CH_3))OC(O)O—R[5], —CH(CH_3)OC(O)O—R[5], —R[5], —CH_2C(O)O—R[5], —CH(CH_3)C(O)O—R[5], CH_2CH_2C(O)O—R[5], —CH_2OP(O)(OCH_3)O—R[5], and —CH_2P(O)(OH)O—R[5].

In another embodiment of the invention, Y is selected from the group consisting of —C((CH_3)(CH_3))OC(O)O—R[5] and —CH(CH_3)OC(O)O—R[5].

In another embodiment of the invention, Y is selected from the group consisting of —C((CH_3)(CH_3))OC(O)O—R[5] and —CH(CH_3)OC(O)O—R[5], wherein R[5] is

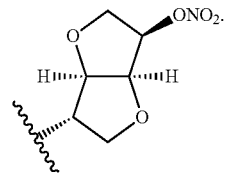

In another embodiment of the invention, Y is selected from the group consisting of —C((CH_3)(CH_3))OC(O)O—R[5] and —CH(CH_3)OC(O)O—R[5], wherein R5 is

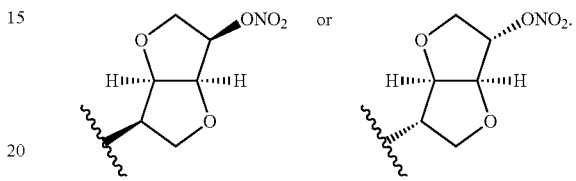

In another embodiment, the compound is selected from the group of compounds consisting of:

1-[({[(3S,6R)-6-(nitrooxy)hexahydrofuro[3,2-b]furan-3-yl]oxy}carbonyl)oxy]-1-methylethyl 2-ethoxy-1-{[2'-(1H-tetrazol-5-yl)biphenyl-4-yl]methyl}-1H-benzimidazole-7-carboxylate, (1S)-1-[({[(3S,3aR,6R,6aS)-6-(nitrooxy)hexahydrofuro[3,2-b]furan-3-yl]oxy}carbonyl)oxy]ethyl 2-butyl-4-chloro-1-{[2'-(1H-tetrazol-5-yl)biphenyl-4-yl]methyl}-1H-imidazole-5-carboxylate, (1R)-1- [({[(3S,3aR,6R,6aS)-6-(nitrooxy)hexahydrofuro[3,2-b]furan-3-yl]oxy}carbonyl)oxy]ethyl 2-butyl-4-chloro-1-{[2'-(1H-tetrazol-5-yl)biphenyl-4-yl]methyl}-1H-imidazole-5-carboxylate, (1S)-1-[({[(3S,3aR,6R,6aS)-6-(nitrooxy)hexahydrofuro[3,2-b]furan-3-yl]oxy}carbonyl)oxy]ethyl 2-ethoxy-1-{[2'-(1H-tetrazol-5-yl)biphenyl-4-yl]methyl}-1H-benzimidazole-7-carboxylate, (1R)-1-[({[(3S,3aR,6R,6aS)-6-(nitrooxy)hexahydrofuro[3,2-b]furan-3-yl]oxy}carbonyl)oxy]ethyl 2-ethoxy1-{[2'-(1H-tetrazol-5-yl)biphenyl-4-yl]methyl}-1H-benzimidazole-7-carboxylate, (1S)-1-[({[(3S,3aR,6R,6aS)-6-(nitrooxy)hexahydrofuro[3,2-b]furan-3-yl]oxy}carbonyl)oxy]ethyl (2S)-3-methyl-2-(pentanoyl{[2'-(1H-tetrazol-5-yl)biphenyl-4-yl]methyl}amino)butanoate, (3S,3aR,6R,6aS)-6-(nitrooxy)hexahydrofuro[3,2-b]furan-3-yl 2-butyl-4-chloro-1-{[2'-(1H tetrazol-5-yl)biphenyl-4-yl]methyl }-1H-imidazole-5-carboxylate, (3S,3aR,6R,6aS)-6-(nitrooxy)hexahydrofuro[3,2-b]furan-3-yl2-ethoxy-1-{[2'-(1H-tetrazol-5-yl)biphenyl-4-yl]methyl}-1H-benzimidazole-7-carboxylate, 2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate, (1R)-1-methyl-2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate, (1S)-1-methyl-2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate, 3-{[(3S,3aR,6R,6aS)-6-(nitrooxy)hexahydrofuro[3,2-]furan-3-yl]oxy}-3-oxopropyl 2-butyl-4-chloro-1-{[2'-(1H-tetrazol-5-yl)biphenyl-4-yl]methyl}-1H-imidazole-5-carboxylate,

[(methoxy{[(3S,3aS,6R,6aS)-6-(nitrooxy)hexahydrofuro[3,2-b]furan-3-yl]oxy}phosphoryl)oxy]methyl 2-butyl-4-chloro-1-{[2'(1H-tetrazol- 5 -yl)biphenyl-4-yl]methyl}-1H-imidazole-5-carboxylate, and (hydroxy {[(3S,3aS,6R,6aS)-6-(nitrooxy)hexahydrofuro[3,2-b]furan-3-yl]oxy}phosphoryl)methyl 2-butyl-4-chloro-1-{[2'-(1H-tetrazol-5-yl)biphenyl-4-yl]methyl}-1H-imidazole-5-carboxylate, or a stereoisomer thereof, or a pharmaceutically acceptable salt thereof, or a pharmaceutically acceptable salt of the stereoisomer thereof.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g., "$\xi$—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S,5S,7S)-N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide, The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably I mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

2-Butyl-4-chloro-1-[(2'-(1-H-tetrazol-5-yl)biphenyl-4-yl) methyl]-imidazole-5-carboxylic acid is the active metabolite of 2-butyl-4-chloro-1-[p-(o-1H-tetrazol-5-ylphenyl)-benzyl] imidazole-5-methanol which is available as a monopotassium salt (also known as losartan potassium salt). Losartan potassium salt is available commercially as the active ingredient in COZAAR® (Merck & Co., Inc. (Whitehouse Station, N.J.)). The preparation of losartan potassium salt is described in U.S. Pat. Nos. 5,138,069, 5,130,439, and 5,310,928. Tetrazolylphenylboronic acid intermediates useful in the synthesis of losartan potassium salt are described in U.S. Pat. No. 5,206,374. Additional patents which describe procedures useful for making losartan include U.S. Pat. Nos. 4,820,843, 4,870,186, 4,874,867, 5,039,814, and 5,859,258.

INTERMEDIATE 1

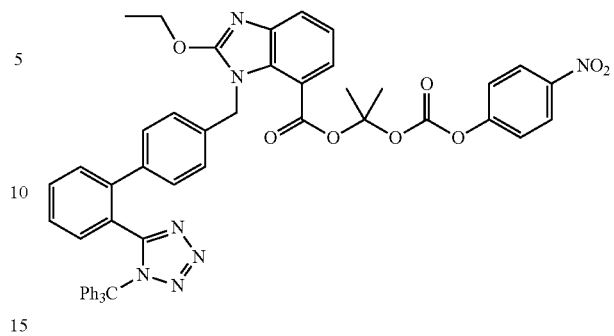

1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate An orange suspension of mercuric oxide (1.17 g, 5.39 mmol) and 2-ethoxy-1-{[2'-(1-trityl-1H-tetrazol-5-yl)biphenyl-4-yl]methyl}-1H-benzimidazole-7-carboxylic acid (7.36 g, 10.8 mmol) in dry tetrahydrofuran (95 mL) was stirred at room temperature for 24 hours. Then 2-chloroisopropyl p-nitrophenyl carbonate (prepared as described in U.S. Pat. No. 5,684,018) (1.40 g, 5.39 mmol) was added, and the reaction was stirred at room temperature for about 7 days and monitored by TLC (hexane/ethyl acetate 6/4). The mixture was diluted with dichloromethane, washed with water, and the organic layer was dried over sodium sulfate and concentrated under reduced pressure. The residue was purified by flash chromatography (Biotage SP1; column 65i; TLC method: n-hexane/ethyl acetate 7/3; $R_f$=0.20), affording the title product.

INTERMEDIATES 2 and 3

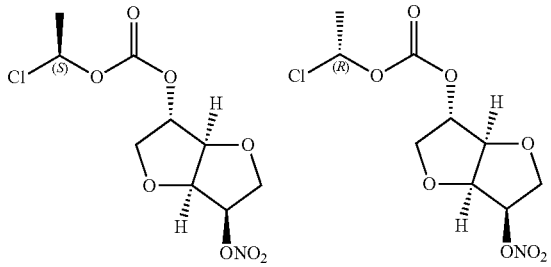

(1S)-1-chloroethyl (3S,3aR,6R,6aS)-6-(nitrooxy) hexahydrofuro[3,2-b]furan-3-yl carbonate and (1R)-1-chloroethyl (3S,3aR,6R,6aS)-6-(nitrooxy)hexahydrofuro[3,2-b]furan-3-yl carbonate Pyridine (13.2 mL, 164 mmol) was added to a solution of isosorbide-5-mononitrate (10.0 g, 52.3 mmol) and 1-chloroethyl chloroformate (6.6 mL, 60.7 mmol) in dichloromethane (209 mL) at room temperature. The solution was stirred for 2 days. Water was added and the solution was extracted with dichloromethane. The combined organic layers were dried (magnesium sulfate), filtered, and concentrated in vacua. The residue was purified by column chromatography on silica gel, eluting with ethyl acetate/hexanes to afford first the (S)-diastereomer followed by the (R)-diastereomer, respectively. (S)-

Diastereomer (Intermediate 2): ¹H NMR (500 MHz, CDCl₃) δ 6.40 (q, J=6.0 Hz, 1H), 5.36 (td, J=5.5, 3.0 Hz, 1H), 5.17 (d, J=2.5 Hz, 1H), 5.00 (t, J=5.5 Hz, 1H), 4.56 (d, J=4.5 Hz, 1H), 4.11 (d, J=8.0 Hz, 1H), 4.02 (t, J=12.5 Hz, 2H), 3.91 (dd, J=11.0, 5.5 Hz, 1H), 1.82 (d, J=6.0 Hz, 3H). (R)-Diastereomer (Intermediate 3): ¹H NMR (500 MHz, CDCl₃) δ 6.40 (q, J=6.0 Hz, 1H), 5.36 (td, J=5.5, 2.0 Hz, 1H), 5.16 (d, J=2.5 Hz, 1H), 4.99 (t, J=5.5 Hz, 1H), 4.54 (d, J=4.5 Hz, 1H), 4.14 (t, J=11.0 Hz, 1H), 4.05-3.99 (m, 2H), 3.91 (dd, J=11.0, 5.5 Hz, 1H), 1.82 (d, J=6.0 Hz, 3H).

INTERMEDIATE 4

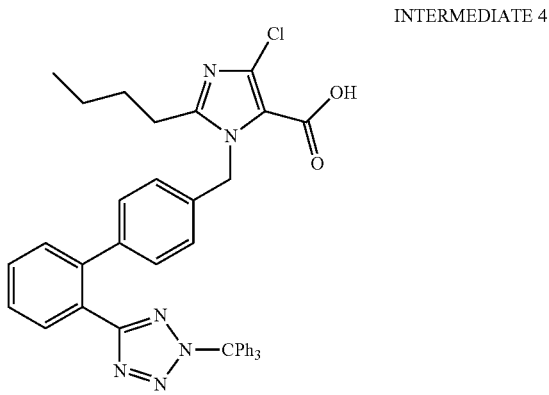

2-butyl-4-chloro-1-{[2'-(1-trityl-1H-tetrazol-5-yl)biphenyl-4-yl]methyl}-1H-imidazole-5-carboxylic acid Step A: (2-butyl-4-chloro-1-[2'-(1H-tetrazol-5-yl)biphenyl-4-yl]methyl)-1H-imidazole-5-carboxylic acid (E3174)

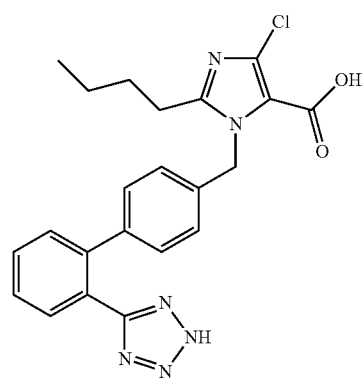 [SMILES: CCCCc1nc(Cl)c(C(=O)O)n1Cc1ccc(-c2ccccc2-c2nn[nH]n2)cc1]

Water (10 L) was added to a 22 L 4-neck round bottom flask. The water was cooled to 0° C. At 0° C., potassium hydroxide (855 g, 15.24 mol) was added followed by losartan potassium (500 g, 1.09 mol)), sodium periodate (554 g, 2.59 mol) and ruthenium (III) chloride hydrate (12 g, 0.05 mol) and the reaction mixture was stirred at 0° C. overnight. The reaction mixture was filtered. IPA (90 mL) was added to the filtrate while stirring. The solution was warmed to 25° C. and stirred for 2.5 hrs. After 2.5 hrs., phosphoric acid (1200 mL) was added, maintaining the temperature below +30° C. The mixture was stirred for 30 min and the product was filtered, washing with water. The residue was dried in the vacuum oven at 55° C. overnight. The solid was dissolved in methanol (4 L) and isopropyl acetate (12 L), and charcoal (activated carbon) (100 g) was added. The mixture was stirred at rt for 3.5 hrs, filtered and concentrated. The product was redissolved in DCM/MeOH and precipitated with heptane to afford the title compound as a greenish/brown foam which was used in subsequent steps without further purification.

Step B: 2-butyl-4-chloro-1-{[2'-(2-trityl-2H-tetrazol-5-yl)biphenyl-4-yl]methyl}-1H-imidazole-5-carboxylic acid

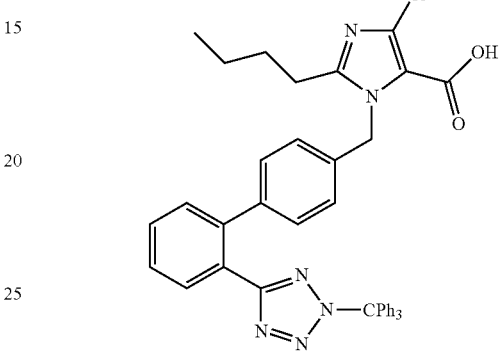

To a solution of E3174 (234.58 g, 0.54 mol) in DCM (4500 mL) was added triethylamine (85 mL, 0.59 mol) followed by a solution of trityl chloride (159 g, 0.56 mol) in DCM (800 mL) and the reaction mixture was stirred at rt overnight. The reaction mixture was washed with water, dried (MgSO4), filtered, and concentrated in vacuo. Chromatography over silica eluting with 20-80% acetone/heptane afforded the title compound as an orange solid.

EXAMPLE 1

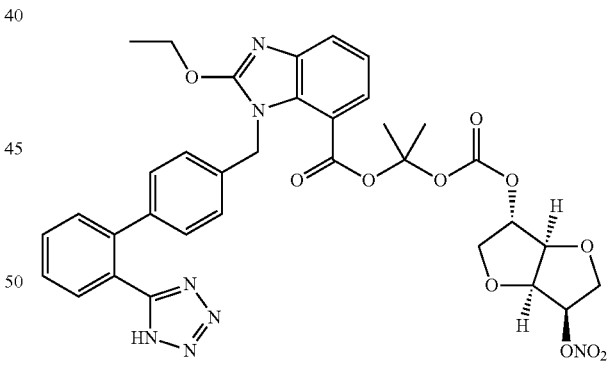

1-[({[(3S,6R)-6-(nitrooxy)hexahydrofuro[3,2-b]furan-3-yl]oxy}carbonyl)oxy]-1-methylethyl 2-ethoxy-1-{[2'-(1H-tetrazol-5-yl)biphenyl-4-yl]methyl}-1H-benzimidazole-7-carboxylate Isosorbide-5-mononitrate (0.203 g, 1.06 mmol) was added to a stirred solution of 1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate (Intermediate 1, 0.800 g, 0.883 mmol), 4-dimethylaminopyridine (0.162 g, 1.33 mmol) and scandium trifluoromethanesulfonate (0.087 g; 0.177 mmol) in dichloromethane (12 mL). The solution was stirred at room temperature for 24 hours. Then the mixture was diluted with dichloromethane, washed with aqueous sodium dihydrogenphosphate (20 mL) and brine (20 mL); the organic layer was dried over sodium sulfate and concentrated under reduced pressure. The residue was purified by flash chromatography (Biotage SP1; column 40+M; TLC method: n-hexane/ethyl acetate: 6/4; $R_f$=0.33) to afford a solid that was dissolved in methanol (8 mL). The mixture was stirred at 40° C. for 5 hours, at 60° C. for 2 hours, and at room temperature for 18 hours. Then the solution was concentrated under reduced pressure. The residue was purified by flash chromatography (Biotage SP1; column 25+M; dichloromethane/methanol: 98/2), affording the title compound as a white solid. $^1$H NMR (300 MHz, CDCl$_3$) δ 8.03 (d, 1H), 7.69-7.58 (m, 2H), 7.48 (d, 1H), 7.31 (d, 1H), 6.88 (t, 1H), 6.80 (d, 2H), 6.76-6.62 (m, 3H), 5.60 (s, 2H), 5.41-5.33 (m, 1H), 5.03 (d, 1H), 4.95 (t, 1H), 4.48 (d, 1H), 4.36-4.15 (m, 2H), 4.10-3.86 (m, 3H), 1.62 (d, 6H) 1.43 (t, 3H).

EXAMPLE 2

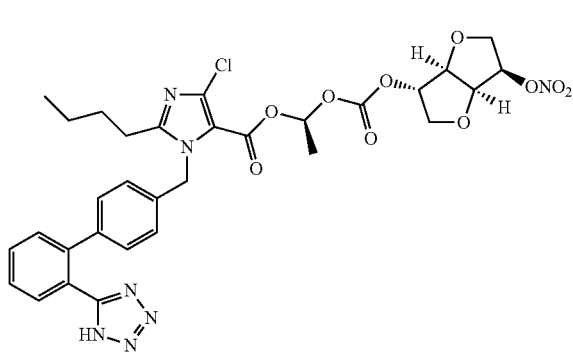

(1S)-1-[({[(3S,3aR,6R,6aS)-6-(nitrooxy)hexahydrofuro[3,2-b]furan-3-yl]oxy}carbonyl)oxy]ethyl 2-butyl-4-chloro-1-{[2'-(1H-tetrazol-5-yl)biphenyl-4-yl]methyl}-1H-imidazole-5-carboxylate Cesium carbonate (5.34 g, 16.4 mmol) was added to a solution of 2-butyl-4-chloro-1-{[2'-(1-trityl-1H-tetrazol-5-yl)biphenyl-4-yl]methyl}-1H-imidazole-5-carboxylic acid (Intermediate 4, 8.56 g, 116 mmol) and (1S)-1-chloroethyl (3S,3aR,6R,6aS)-6-(nitrooxy)hexahydrofuro[3,2-b]furan-3-yl carbonate (Intermediate 2, 3.75 g, 12.6 mmol) in N,N-dimethylformamide (126 mL). The mixture was heated to 70° C. for 2 hours. Water was added and the solution was extracted with ethyl acetate (2×). The combined organic layers were dried (magnesium sulfate), filtered, and concentrated in vacua. The residue was purified by flash chromatography, eluting with 0-100% ethyl acetate in hexanes to give a yellow foam that was subsequently dissolved in methanol (106 mL). The solution was stirred at 70° C. for 2 hours and then concentrated in vacuo. The residue was purified by HPLC reverse phase (C-18), eluting with acetonitrile/water +0.1% trifluoroacetic acid to give the title compound. $^1$H NMR (500 MHz, CDCl$_3$) δ 8.00 (d, J=7.5 Hz, 1H), 7.61 (t, J=7.5 Hz, 1H), 7.54 (t, J=7.5 Hz, 1H), 7.43 (d, J=8.0 Hz, 1H), 7.15 (d, J=8.0 Hz, 2H), 6.95 (d, J=8.0 Hz, 2H), 6.85 (q, J=5.5 Hz, 1H), 5.55 (d, J=16.5 Hz, 1H), 5.45 (d, J=16.5 Hz, 1H), 5.27 (td, J=5.5, 3.0 Hz, 1H), 5.03 (d, J=3.0 Hz, 1H), 4.84 (t, J=5.5 Hz, 1H), 4.39 (d, J=5.5 Hz, 1H), 4.00 (d, J=11.0 Hz, 1H), 3.95-3.88 (m, 2H), 3.78 (dd, J=11.0, 5.5 Hz, 1H), 2.66 (t, J=8.0 Hz, 2H), 1.68 (quintet, J=8.0 Hz, 2H), 1.60 (d, J=5.5 Hz, 3H), 1.36 (sextet, J=8.0 Hz, 2H), 0.89 (t, J=8.0 Hz, 3H); LC-MS: m/z 698.2 (M+H).

EXAMPLE 3

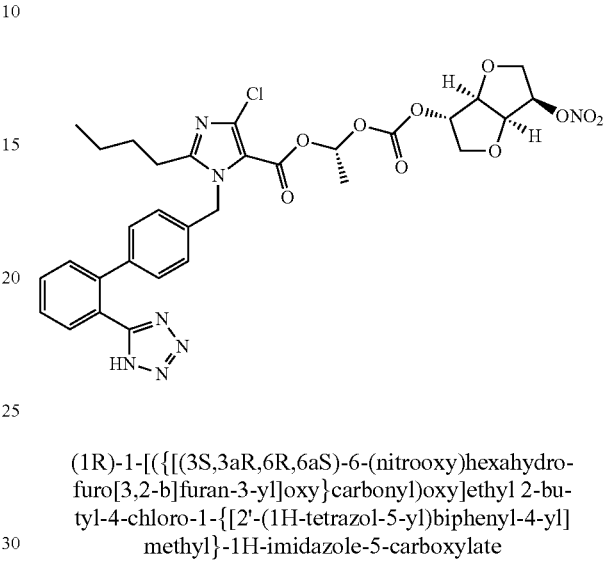

(1R)-1-[({[(3S,3aR,6R,6aS)-6-(nitrooxy)hexahydrofuro[3,2-b]furan-3-yl]oxy}carbonyl)oxy]ethyl 2-butyl-4-chloro-1-{[2'-(1H-tetrazol-5-yl)biphenyl-4-yl]methyl}-1H-imidazole-5-carboxylate The title compound was prepared by following the procedure for example 2, except that the reagent (1S)-1-chloroethyl (3S,3aR,6R,6aS)-6-(nitrooxy)hexahydrofuro[3,2-b]furan-3-yl carbonate (Intermediate 2) was replaced by (1R)-1-chloroethyl (3S,3aR,6R,6aS)-6-(nitrooxy)hexahydrofuro[3,2-b]furan-3-yl carbonate (Intermediate 3). $^1$H NMR (500 MHz, CDCl$_3$) δ 7.97 (d, J=7.5 Hz, 1H), 7.61 (t, J=7.5 Hz, 1H), 7.54 (t, J=7.5 Hz, 1H), 7.43 (d, J=8.0 Hz, 1H), 7.14 (d, J=8.0 Hz, 2H), 6.94 (d, J=8.0 Hz, 2H), 6.85 (q, J=5.5 Hz, 1H), 5.54 (d, J=16.5 Hz, 1H), 5.48 (d, J=16.5 Hz, 1H), 5.30 (td, J=5.5, 3.0 Hz, 1H), 5.02 (d, J=3.0 Hz, 1H), 4.90 (t, J=5.5 Hz, 1H), 4.56 (d, J=5.5 Hz, 1H), 4.03 (d, 11.0 Hz, 1H), 3.96-3.89 (m, 2H), 3.83 (dd, J=11.0, 5.5 Hz, 1H), 2.64 (t, J=8.0 Hz, 2H), 1.65 (quintet, J=8.0 Hz, 2H), 1.59 (d, J=5.5 Hz, 3H), 1.34 (sextet, J=8.0 Hz, 2H), 0.87 (t, J=8.0 Hz, 3H); LC-MS: m/z 698.2 (M+H).

EXAMPLE 4

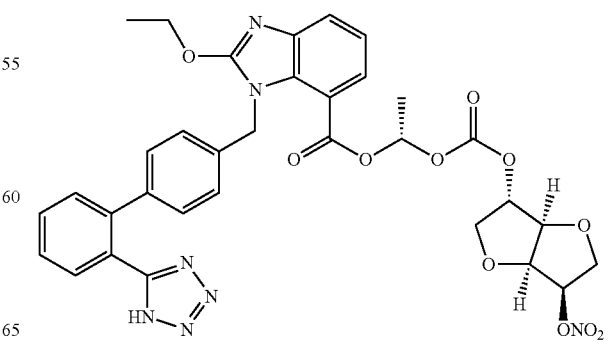

(1S)-1-[({[(3S,3aR,6R,6aS)-6-(nitrooxy)hexahydro-furo[3,2-b]furan-3-yl]oxy}carbonyl)oxy]ethyl 2-ethoxy-1-{[2'-(1H-tetrazol-5-yl)biphenyl-4-yl]methyl}-1H-benzimidazole-7-carboxylate The title compound was prepared by following the procedure for example 2, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 7.91 (d, J=7.1 Hz, 1H), 7.62-7.58 (m, 2H), 7.40 (d, J=7.8 Hz, 1H), 7.27 (d, J=8.0 Hz, 1H), 6.86 (t, J=7.9 Hz, 1H), 6.77 (d, J=7.8 Hz, 2H), 6.74-6.68 (m, 1H), 6.65 (d, J=7.6 Hz, 2H), 6.61 (q, J=5.3 Hz, 1H), 5,55 (s, 2H), 5.36 (td, J=5.4, 2.5 Hz, 1H), 5.02 (d, J=2.5 Hz, 1H), 4.83 (t, J=5.3 Hz, 1H), 4.44 (d, J=4.8 Hz, 1H), 4.36-4.26 (m, 1H), 4.14-4.04 (m, 1H), 4.03 (d, J=11.2 Hz, 1H), 3.98 (dd, J=11.4, 2.3 Hz, 1H), 3.92 (dd, J=10.6, 2.9 Hz, 1H), 3.89 (dd, J=11.5, 5.3 Hz, 1H), 1.40 (t, J=7.1 Hz, 3H), 1.26 (d, J=4.8 Hz, 3H); LC-MS: m/z 702.1 (M+H).

EXAMPLE 5

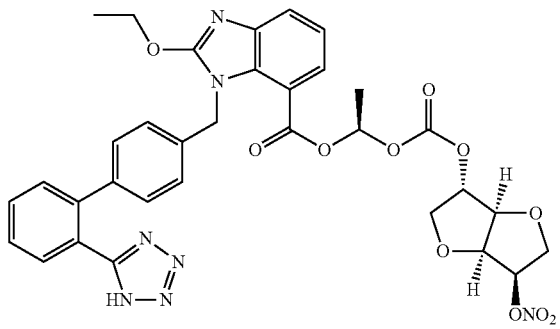

(1R)-1-[({[(3S,3aR,6R,6aS)-6-(nitrooxy)hexahydro-furo[3.2-b]furan-3-yl]oxy)}carbonyl)oxy]ethyl 2-ethoxy-1-{[2'-(1H-tetrazol-5-yl)biphenyl-4-yl]methyl}-1H-benzimidazole-7-carboxylate The title compound was prepared by following the procedure for example 3, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 7.98 (dd, J=7.4, 1.5 Hz, 1H), 7.61 (td, J=7.5, 1.5 Hz, 1H), 7.58 (td, J=7.5, 1.7 Hz, 1H), 7.45 (d, J=7.7 Hz, 1H), 7.28 (dd, J=7.6, 1.1 Hz, 1H), 6.89 (t, J=7.9 Hz, 1H), 6.82-6.74 (m, 3H), 6.69 (d, J=7.7 Hz, 2H), 6.63 (q, J=5.4Hz, 1H), 5.62 (d, J=17 Hz, 1H), 5.56 (d, J=16.9 Hz, 1H), 5.33 (td, J=5,5, 2.8 Hz, 1H), 5.03 (d, J=2.9 Hz, 1H), 4.84 (t, J=5.3 Hz, 1H), 4.36 (d, J=5.0 Hz, 1H), 4.34-4.26 (m, 1H), 4.18-4.10 (m, 1H), 4.02- 3.96 (m, 2H), 3.94-3.86 (m, 2H), 1.41 (t, J=7.1 Hz, 3H), 1.32 (d, J=5.3 Hz, 3H); LC-MS: m/z 702.1 (M+H).

EXAMPLE 6

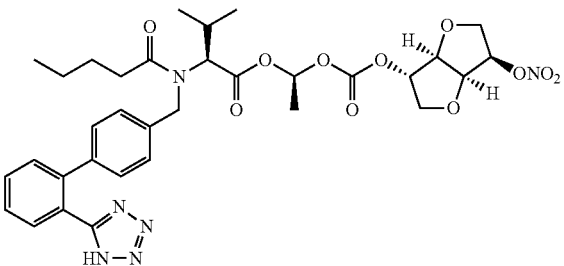

(1S)-1-[({[(3S,3aR,6R,6aS)-6-(nitrooxy)hexahydro-furo[3,2-b]furan-3-yl]oxy}carbonyl)oxy]ethyl (2S)-3-methyl-2-(pentanoyl{[2'-(1H-tetrazol-5-yl)biphenyl-4-yl]methyl}amino)butanoate The title compound was prepared by following the procedure for example 2, except that the reagent 2-butyl-4-chloro-1-{[2'-(1-trityl-1H-tetrazol-5-yl)biphenyl-4-yl]methyl}-1H-imidazole-5-carboxylic acid was replaced by commercially available (2S)-3-methyl-2-(pentanoyl{[2'-(1-trityl-1H-tetrazol-5-yl)biphenyl-4-yl]methyl}amino)butanoic acid. LC-MS: m/z 719.4 (M+Na).

EXAMPLE 7

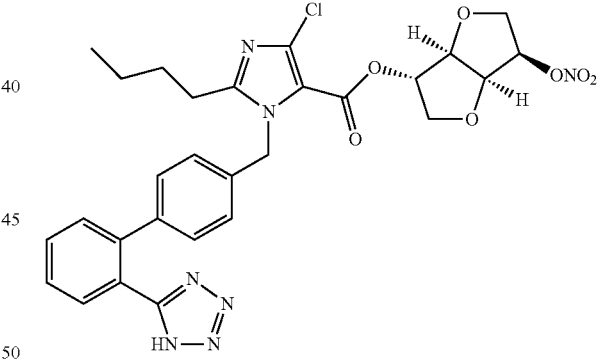

(3S,3aR,6R,6aS)-6-(nitrooxy)hexahydrofuro[3,2-b]furan-3-yl 2-butyl-4-chloro-1-{[2'-(1H-tetrazol-5-yl)biphenyl-4-yl]methyl}-1H-imidazole-5-carboxylate A mixture of 2-butyl-4-chloro-1-{[2'-(1H-tetrazol-5-yl)biphenyl-4-yl]methyl}-1H-imidazole-5-carboxylic acid (Step A, Intermediate 4, 7.83 g, 16.5 mmol), isosorbide-5-mononitrate (1.55 g, 8.11 mmol), 1-ethyl-3-(3-dimethylaminopropyl)carbodiimide hydrochloride (3.78 g, 19.7 mmol), 1-hydroxybenzotriazole (1.25 g, 8.16 mmol), 4-dimethylaminopyridine (0.10 g, 0.82 mmol), and N-methylmorpholine (9.0 mL, 82 mmol) was dissolved in dichloromethane (150 mL) and stirred for 2 days. It was then concentrated in vacuo and purified by reversed-phase massdirected HPLC (Sunfire C-18) to afford the title compound. $^1$H NMR (500 MHz, CDCl$_3$) δ 8.02 (dd, J=7.6, 1.0 Hz, 1H), 7.61 (td, J=7.6, 1.3 Hz, 1H), 7.55 (td, J=7.7, 1.1 Hz, 1H), 7.43 (d, J=7.8 Hz, 1H), 7.18 (d, J=7.7 Hz, 2H), 6.96 (d, J=7.8 Hz, 2H), 5.50 (s, 2H), 5.40 (td, J=5.4, 3.0 Hz, 1H), 5.32-5.30 (m, 1H), 4.99 (t, J=5.2 Hz, 1H), 4.51 (d, J=5.0 Hz, 1H), 4.06-4.02 (m, 3H), 3.99 (dd, J=11.4, 5.4 Hz, 1H), 2.68 (t, J=7.7 Hz, 2H), 1.69 (quintet, J=7.7 Hz, 2H), 1.36 (sextet, J=7.5 Hz, 2H), 0.89 (t, J=7.3 Hz, 3H); LC-MS: m/z 610.1 (M+H).

EXAMPLE 8

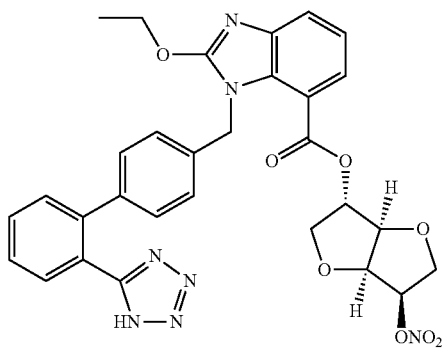

(3S,3aR,6R,6aS)-6-(nitrooxy)hexahydrofuro[3,2-b]furan-3-yl 2-ethoxy-1-{[2'-(1H-tetrazol-5-yl)biphenyl-4-yl]methyl}-1H-benzimidazole-7-carboxylate The title compound was prepared by following the procedure for example 7, except that the reagent 2-butyl-4-chloro-1-{[2'-(1H-tetrazol-5-yl)biphenyl-4-yl]methyl}-1H-imidazole-5-carboxylic acid was replaced by commercially available 2-ethoxy-1-{[2'-(1H-tetrazol-5-yl)biphenyl-4-yl]methyl}-1H-benzimidazole-7-carboxylic acid. $^1$H NMR (500 MHz, CDCl$_3$) δ 7.93 (d, J=7.3 Hz, 1H), 7.66-7.57 (m, 2H), 7.41 (t, J=4.4 Hz, 1H), 7.32 (d, J=7.3 Hz, 1H), 7.00-6.90 (m, 2H), 6.84 (d, J=7.8 Hz, 2H), 6.68 (d, J=7.3 Hz, 2H), 5.62 (s, 2H), 5.24-5.18 (m, 1H), 5.08 (d, J=2.5 Hz, 1H), 4.87 (t, J=4.8 Hz, 1H), 4.40-4.30 (m, 2H), 4.20-4.10 (m, 1H), 3.92 (dd, J=11.2, 2.7 Hz, 1H), 3.80 (dd, J=11.1, 2.6 Hz, 1H), 3.76 (dd, J=11.3, 5.8 Hz, 1H), 3.54-3.42 (m, 1H), 1.40 (t, J=7.1 Hz, 3H); LC-MS: m/z 614.2 (M+H).

EXAMPLE 9

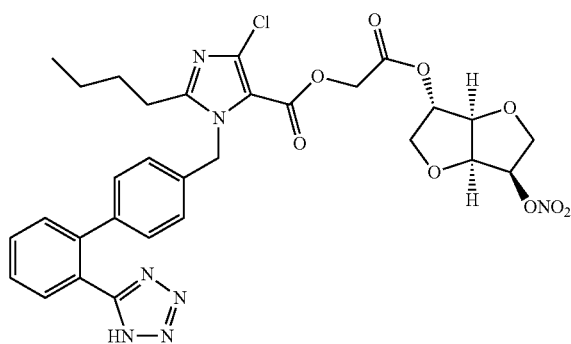

2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate Step A: 2-Ethoxy-2-oxoethyl 2-butyl-4-chloro-1-{[2'-(1-trityl-1H-tetrazol-5-yl)biphenyl-4-yl]methyl}-1H-imidazole-5-carboxylate Ethyl bromoacetate (263 µL, 2.37 mmol) was added to a solution of 2-butyl-4-chloro-1-{[2'-(1-trityl-1H-tetrazol-5-yl)biphenyl-4-yl]methyl}-1H-imidazole-5-carboxylic acid (Intermediate 4, 1000 mg, 1.48 mmol), and potassium carbonate (347 mg, 2,51 mmol) in N,N-dimethylformamide (10 mL). The solution was stirred for 2 hours at room temperature. Water was added and the solution was extracted with diethyl ether (2x). The organic layers were dried (magnesium sulfate), filtered, and concentrated in vacuo. The residue was used crude in the following step. LC-MS: m/z 787.1 (M+Na).

Step B: {[(2-butyl-4-chloro-1-{[2'-(1H-tetrazol-5-yl)biphenyl-4-yl]methyl}-1H-imidazol-5-yl)carbonyl]oxy}acetic acid 2-Ethoxy-2-oxoethyl 2-butyl-4-chloro-1-{[2'-(1-trityl-1H-tetrazol-5-yl)biphenyl-4-yl]methyl}-1H-imidazole-5-carboxylate (1130 mg, 1.48 mmol) was dissolved in concentrated hydrochloric acid (24 mL). The solution was stirred at 100° C. for 30 minutes. The solution was washed with diethyl ether (2x) and the aqueous layer was concentrated in vacuo. The residue was used crude in the following step. LC-MS: m/z 495.0 (M+H).

Step C: 2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate The title compound was prepared by following the procedure for example 7, except that the reagent 2-butyl-4-chloro-1-{[2'-(1H-tetrazol-5-yl)biphenyl-4-yl]methyl)-1H-imidazole-5-carboxylic acid was replaced by {[(2-butyl-4-chloro-1-([2'-(1H-tetrazol-5-yl)biphenyl-4-yl]methyl}-1H-imidazol-5-yl)carbonyl]oxy}acetic acid. $^1$H NMR (500 MHz, CDCl$_3$) δ 8.41-7.99 (m, 1H), 7.60 (t, J =7.5 Hz, 1H), 7.54 (t, J =7.5 Hz, 1H), 7.42 (d, J =7.5 Hz, 1H), 7.15 (d, J=7.5 Hz, 2H), 6.96 (d, J=7.5 Hz, 2H), 5.53 (d, J=16.5 Hz, 1H), 5.49 (d, J=16.5 Hz, 1H), 5.33-5.29 (m, 1H), 5.21 (d, J=3.0 Hz, 1H), 4.92 (t, J=5.5 Hz, 1H), 4.78 (d, J=16.0 Hz, 1H), 4.72 (d, J=16.0 Hz, 1H), 4.45 (d, J=5.0 Hz, 1H), 3.99 (t, J=11.0 Hz, 1H), 3.93 (td, J=11.0, 3.0 Hz, 2H), 3.82 (dd, J=11.0, 5.0 Hz, 1H) 2.67 (t, J=7.5 Hz, 2H), 1.67 (quintet, J=7.5 Hz, 2H), 1.35 (sextet, J=7.5 Hz, 2H), 0.88 (t, J=7.5 Hz, 3H); LC-MS: m/z 668.1 (M+H).

EXAMPLE 10

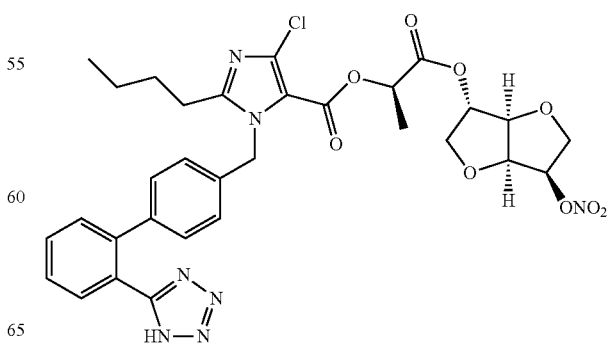

(1R)-1-methyl-2-{[(3S,3aR,6R,6aS)-6-(nitrooxy)
hexahydrofuro[3,2-b]furan-3-yl]oxy}-2-oxoethyl
2-butyl-4-chloro-1-{[2'-(1H-tetrazol-5-yl)biphenyl-
4-yl]methyl}-1H-imidazole-5-carboxylate Step A: (1R)-2-(benzyloxy)-1-methyl-2-oxoethyl
2-butyl-4-chloro-1-{[2'-(1H-tetrazol-5-yl)biphenyl-
4-yl]methyl}-1H-imidazole-5-carboxylate The title compound was prepared by following the procedure for example 7, except that the reagent isosorbide-5-mononitrate was replaced by (R)-lactic acid benzyl ester. $^1$H NMR (500 MHz, CDCl$_3$) δ 8.09 (d, J=7.5 Hz, 1H), 7.58 (t, J=7.5 Hz, 1H), 7.53 (t, J=7.5 Hz, 1H), 7.40 (d, J=7.0 Hz, 1H), 7.32-7.24 (m, 5H), 7.13 (d, J=8.0 Hz, 21-1), 6.93 (d, J=8.0 Hz, 2H), 5.50 (d, J=16.0 Hz, 1H), 5.45 (d, J=16.0 Hz, 1H), 5.19 (q, J=7.0 Hz, 1H), 5.11 (s, 2H), 2.69 (t, J=8.0 Hz, 2H), 1.72 (quintet, J=7.5 Hz, 2H), 1.55 (d, J=7.0 Hz, 3H) 1.39 (sextet, J=7.5 Hz, 2H), 0.91 (t, J=7.5 Hz, 3H); LC-MS: m/z 599.2 (M+H).

Step B: (2R)-2-{[(2-butyl-4-chloro-1-{[2'-(1H-tetrazol-5-yl)biphenyl-4-yl]methyl}-1H-imidazol-5-yl)carbonyl]oxy}propanoic acid 10% Palladium on carbon (59 mg, 0.55 mmol) was added to a stirred ethanol (5.5 mL) solution of (1R)-2-(benzyloxy)-1-methyl-2-oxoethyl 2-butyl-4-chloro-1-{[2'-(1H-tetrazol-5-yl)biphenyl-4-yl]methyl}-1H-imidazole-5-carboxylate (332 mg, 0.55 mmol). The mixture was stirred under hydrogen for 2 hours. The mixture was filtered through Celite, and the filtrate was concentrated in vacuo to give the title compound as a white solid. $^1$H NMR (500 MHz, CDCl$_3$) δ 7.67-7.62 (m, 2H), 7.56-7.50 (m, 2H), 7.09 (d, J=8.0 Hz, 2H), 7.01 (d, J=8.0 Hz, 2H), 5.67 (d, J=16.5 Hz, 1H), 5.57 (d, J=16.5 Hz, 1H), 5.15 (q, J=6.5 Hz, 1H), 2.65 (t, J=7.5 Hz, 2H), 1.56 (quintet, J=7.5 Hz, 2H), 1.49 (d, J=7.0 Hz, 3H), 1.31 (sextet, J=7.5 Hz, 2H), 0.87 (t, J=7.5 Hz, 3H); LC-MS: m/z 509.2 (M+H).

Step C: (1R)-1-methyl-2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate The title compound was prepared by following the procedure for example 7, except that the reagent {[(2-butyl-4-chloro-1-{[2'-(1H-tetrazol-5-yl)biphenyl-4-yl]methyl}-1H-imidazol-5-yl)carbonyl]oxy}acetic acid was replaced by (2R)-2-{[(2-butyl-4-chloro-1-{[2'-(1H-tetrazol-5-yl)biphenyl-4-yl]methyl}-1H-imidazol-5-yl)carbonyl]oxy}propanoic acid. $^1$H NMR (500 MHz, CD$_3$OD) δ 7.68-7.63 (m, 2H), 7.58-7.52 (m, 2H), 7.10 (d, J=8.0 Hz, 2H), 7.04 (d, J=8.0 Hz, 2H), 5.63 (d, J=16.5 Hz, 1H), 5.54 (d, J=16.5 Hz, 1H), 5.42 (td, J=5.5, 2.0 Hz, 1H), 5.21 (d, J=2.5 Hz, 1H), 5.16 (q, J=7.0 Hz, 1H), 4.90 (t, J=5.0 Hz, 1H), 4.44 (d, J=5.0 Hz, 1H), 4.00-3.85 (m, 4H), 2.66 (t, J=7.0 Hz, 2H), 1.57 (quintet, J=7.0 Hz, 2H), 1.50 (d, J=7.5 Hz, 3H), 1.31 (sextet, J=7.0 Hz, 2H), 0.87 (t, J=7.5 Hz, 3H); LC-MS: m/z 682.2 (M+H).

EXAMPLE 11

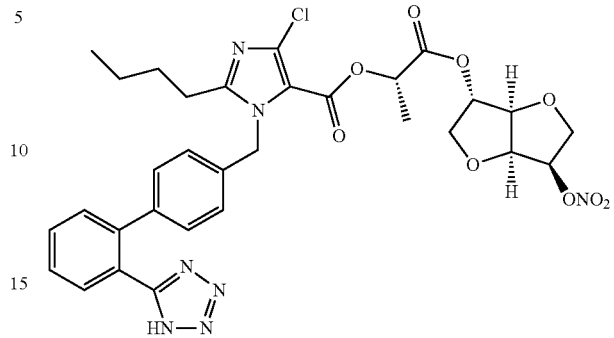

(1S)-1-methyl-2-{[(3S,3aR,6R,6aS)-6-(nitrooxy)
hexahydrofuro[3,2-b]furan-3-yl]oxy}-2-oxoethyl
2-butyl-4-chloro-1-{[2'-(1H-tetrazol-5-yl)biphenyl-
4-yl]methyl}-1H-imidazole-5-carboxylate The title compound was prepared by following the procedure for example 10, except that the reagent (R)-lactic acid benzyl ester was replaced by (S)-lactic acid benzyl ester. $^1$H NMR (500 MHz, CD$_3$OD) δ 7.68-7.62 (m, 2H), 7.57-7.51 (m, 2H), 7.10 (d, J=8.0 Hz, 2H), 6.99 (d, J=8.0 Hz, 2H), 5.63 (d, J=16.5 Hz, 1H), 5.56 (d, J=16.5 Hz, 1H), 5.41 (td, J=5.5, 2.0 Hz, 1H), 5.20-5.13 (m, 2H), 4.90 (t, J=5.0 Hz, 1H), 4.27 (d, J=5.5 Hz, 1H), 3.99-3.84 (m, 4H), 2.66 (t, J=7.5 Hz, 2H), 1.57 (quintet, J=7.0 Hz, 2H), 1.48 (d, J=7.0 Hz, 3H), 1.31 (sextet, J=7.0 Hz, 2H), 0.87 (t, J=7.0 Hz, 3H); LC-MS: m/z 682.2 (M+H).

EXAMPLE 12

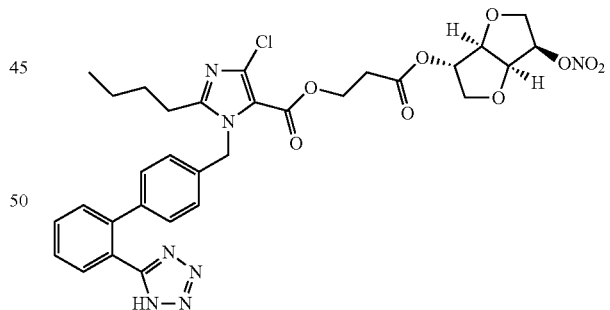

3-{[(3S,3aR,6R,6aS)-6-(nitrooxy)hexahydrofuro[3,
2-b]furan-3-yl]oxy}-3-oxopropyl 2-butyl-4-chloro-1-
{[2'-(1H-tetrazol-5-yl)biphenyl-4-yl]methyl}-1H-
imidazole-5-carboxylate Step A: benzyl 3-hydroxypropanoate β-Propiolactone (5 g, 25 mmol) was added slowly to a stirred solution of sodium methoxide (0.18 g, 3.5 mmol) in benzyl alcohol (45 g, 420 mmol) at 0° C. Stirring was continued for a further 2 hours at 0° C. Then the mixture was warmed to room temperature. After stirred for 7 hours, the reaction mixture was washed with water, dried and distilled to give the title compound. $^1$H NMR (300 MHz, CDCl$_3$): δ 7.33 (m, 5H), 5.13 (s, 2H), 3.86 (t, J=5.6 Hz, 2H), 2.59 (m, 2H).

Step B: 3-{[(3S,3aR,6R,6aS)-6-(nitrooxy)hexahydrofuro[3,2-b]furan-3-yl]oxy}-3-oxopropyl 2-butyl-4-chloro-1-{[2'-(1H-tetrazol-5-yl)biphenyl-4-yl]methyl}-1H-imidazole-5-carboxylate The title compound was prepared by following the procedure for example 10, except that the reagent (R)-lactic acid benzyl ester was replaced by benzyl 3-hydroxypropanoate, LC-MS: m/z 682.0 (M+H).

EXAMPLE 13

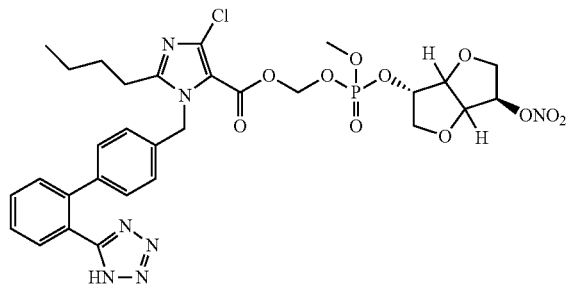

[(methoxy{[(3S,3aS,6R,6aS)-6-(nitrooxy)hexahydrofuro[3,2-b]furan-3-yl]oxy}phosphoryl)oxy]methyl 2-butyl-4-chloro-1-{[2'-(1H-tetrazol-5-yl)biphenyl-4-yl]methyl}-1H-imidazole-5-carboxylate Step A: dimethyl (3S,3aS,6R,6aS)-6-(nitrooxy) hexahydrofuro[3,2-b]furan-3-yl phosphate Trimethyl phosphite (2.95 mL, 25.0 mmol) was added dropwise over ca. 1 hour to a stirred 0° C. mixture of isosorbide-5-mononitrate (3.82 g, 20.0 mmol) and carbon tetrabromide (7.30 g, 22.0 mmol) in pyridine (10 mL), and the mixture was stirred at room temperature for 3 hours. The reaction was partitioned between 1M hydrochloric acid and diethyl ether/ethyl acetate (1:1). The aqueous phase was extracted with diethyl ether. The combined organic extracts were washed with saturated aqueous sodium hydrogen carbonate and brine, dried (sodium sulfate), filtered and concentrated in vacuo. Chromatography over silica eluting with 50-100% ethyl acetate/hexane afforded the title compound as an orange solid. $^1$H NMR (500 MHz, CD$_3$OD) δ 5.46 (td, J=5.5, 2.2 Hz, 1H), 5.02 (t, J=5.3 Hz, 1H), 4.82 (dd, J=6.8, 2.7 Hz, 1H), 4.58 (d, J=5.1 Hz, 1H), 4.10 (d, J=10.7 Hz, 1H), 3.99 (dd, J=11.5, 2.1 Hz, 1H), 3.91 (dd, J=11.4, 5.2 Hz, 1H), 3.88 (dt, J=11.0, 2.4 Hz, 1H), 3.80 (d, J=2.7 Hz, 3H), 3.78 (d, J=2.7 Hz, 3H); LC-MS: m/z 300.0 (M+H).

Step B: methyl (3S,3aS,6R,6aS)-6-(nitrooxy)hexahydrofuro[3,2-b]furan-3-yl hydrogen phosphate Bromotrimethylsilane (0.191 mL, 1.47 mmol) was added to a stirred room temperature mixture of dimethyl (3S,3aS,6R,6aS)-6-(nitrooxy)hexahydrofuro[3,2-b]furan-3-yl phosphate (400 mg, 1.34 mmol) in acetonitrile (6 mL) at 0° C., and the mixture was stirred at room temperature for 1 hour. Methanol (5 mL) was added, and the solution was concentrated. The residue was purified by preparative HPLC, eluting with 10-100% acetonitrile/water+0.1% trifluoroacetic acid, to afford the title compound as a white gum. $^1$H NMR (500 MHz, CD$_3$OD) δ 5.45 (tt, J=5.3, 2.6 Hz, 1H), 5.00 (q, J=5.4 Hz, 1H), 4.74 (ddd, J=9.7, 7.2, 2.8 Hz, 1H), 4.57 (d, J=4.9 Hz, 1H), 4.09 (d, J=10.5 Hz, 1H), 3.97 (dt, J=11.3, 2.5 Hz, 1H), 3.92-3.83 (m, 2H), 3.72 (d, J=11.2 Hz, 3H); LC-MS: m/z 286.0 (M+H).

Step C: chloromethyl methyl (3S,3aS,6R,6aS)-6-(nitrooxy)hexahydrofuro[3,2-b]furan-3-yl phosphate Sodium bicarbonate (289 mg, 3.44 mmol) followed by tetrabutylammonium hydrogensulfate (29.2 mg, 0.086 mmol) were added to a vigorously stirred 0° C. mixture of methyl (3S,3aS,6R,6aS)-6-(nitrooxy)hexahydrofuro[3,2-b]furan-3-yl hydrogen phosphate (245 mg, 0.859 mmol) in dichloromethane (5 mL) and water (7.5 mL), and the mixture was stirred at 0° C. for 10 minutes. Chloromethyl chlorosulfate (0.106 mL, 1.03 mmol) in dichloromethane (2.5 mL) was added, and the mixture was stirred at room temperature for overnight. The organic phase was removed, dried and concentrated. Chromatography over silica, eluting with 20-60% ethyl acetate/hexane afforded the title compound as a colorless oil. $^1$H NMR (500 MHz, CDCl$_3$) δ 5.72-5.64 (m, 2H), 5.36 (td, J=5.5, 2.8 Hz, 1H), 5.02 (t, J=5.2 Hz, 1H), 4.93 (quintet, J=3.6 Hz, 1H), 4.63 (dd, J=12.1, 4.8 Hz, 1H), 4.18 (dd, J=11.0, 7.3 Hz, 1H), 4.00 (dd, J=11.4, 2.8 Hz, 1H), 3.94 (dq, J=11.1, 2.4 Hz, 1H), 3.90 (dd, J=11.3, 5.6 Hz, 1H), 3,83 (d, J=11.4 Hz, 3H); LC-MS: m/z 334.0 (M+H).

Step D: [(methoxy{[(3S,3aS,6R,6aS)-6-(nitrooxy) hexahydrofuro[3,2-b]furan-3-yl]oxy}phosphoryl) oxy]methyl 2-butyl-4-chloro-1-{[2'-(1-trityl-1H-tetrazol-5-yl)biphenyl-4-yl]methyl}-1H-imidazole-5-carboxylate Cesium carbonate (29.3 mg, 0,090 mmol) was added to a stirred, room temperature mixture of chloromethyl methyl (3S,3aS,6R,6aS)-6-(nitrooxy)hexahydrofuro[3,2-b]furan-3-yl phosphate (30 mg, 0.090 mmol) and 2-butyl-4-chloro-1-{[2'-(1-trityl-1H-tetrazol-5-yl)biphenyl-4-yl]methyl}-1H-imidazole-5-carboxylic acid (Intermediate 4, 61.1 mg, 0.090 mmol) in N,N-dimethylformamide and the mixture was stirred at room temperature for overnight. The reaction was cooled, quenched with water and extracted with ethyl acetate. The organic phase was washed with saturated brine, dried (sodium sulfate), filtered and concentrated in vacua. Chromatography over silica, eluting with 40-100% ethyl acetate/hexane afforded the separated diastereomers.

D1: $^1$H NMR (500 MHz, CD$_3$OD) δ 7.81 (dd, J=7.6, 1.2 Hz, 1H), 7.54 (td, J=7.5, 1.3 Hz, 1H), 7.48 (td, J=7.6, 1.1 Hz, 1H), 7.39 (d, 7.7 Hz, 1H), 7.35 (t, J=7.3 Hz, 3H), 7.27 (t, 7.7 Hz, 6H), 7.06 (d, J=8.2 Hz, 2H), 6.91 (d, J=8.0 Hz, 6H), 6.88 (d, J=8.0 Hz, 2H), 5.73 (d, J=14.4 Hz, 2H), 5.57 (d, J=16.5 Hz, 1H), 5.52 (d, J=16.4 Hz, 1H), 5.35 (td, J=5.4, 2.2 Hz, 1H), 4.86 (t, J=5.2 Hz, 1H), 4.80 (dd, J=6.8, 2.7 Hz, 1H), 4.48 (d, J=5.1 Hz, 1H), 4.02 (d, J=11.0 Hz, 1H), 3.87 (dd, J=11.7, 1.8 Hz, 1H), 3.83 (d, J=11.5 Hz, 1H), 3.77 (dt, J=11.3, 2.4 Hz, 1H), 3.73 (d, J=11.4 Hz, 3H), 2.54 (t, J=7.7 Hz, 2H), 1.53 (quintet, J=7.6 Hz, 2H), 1.23 (sextet, J=7.5 Hz, 2H), 0.82 (t, J=7.3 Hz, 3H); LC-MS: m/z 976.3 (M+H).

D2: $^1$H NMR (500 MHz, CD$_3$OD) δ 7.81 (dd, J=7.7, 1.0 Hz, 1H), 7.54 (td, J=7.5, 1.3 Hz, 1H), 7.48 (td, J=7.6, 1.1 Hz, 1H), 7.38 (d, J=7.8 Hz, 1H), 7.35 (t, J=7.4 Hz, 3H), 7.27 (t, J=7.7 Hz, 6H), 7.06 (d, J=8.2 Hz, 2H), 6.90 (d, J=7.6 Hz, 6H), 6.86 (d, J=8.2 Hz, 2H), 5.73 (dd, J=11.8, 5.6 Hz, 1H), 5.71 (dd, J=12.3 Hz, 5.7 Hz, 1H), 5.56 (d, J=16.5 Hz, 1H), 5.50 (d,

J=16.5 Hz, 1H), 5.37 (td, J=5.5, 2.1 Hz, 1H), 4.86 (t, J=5.3 Hz, 1H), 4.80 (dd, J=7.0, 2.7 Hz, 1H), 4.51 (d, J=4.8 Hz, 1H), 3.99 (d, J=11.0 Hz, 1H), 3.89 (dd, J=11.6, 2.0 Hz, 1H), 3.80 (dd, J=11.5, 5.3 Hz, 1H), 3.75 (dt, J=11.1, 2.2 Hz, 1H), 3.73 (d, J=11.5 Hz, 3H), 2.54 (t, J=7.7 Hz, 2H), 1.53 (quintet, J=7.7 Hz, 2H), 1.22 (sextet, J=7.4 Hz, 2H), 0.81 (t, J=7.4 Hz, 3H); LC-MS: m/z 976.3 (M+H).

Step E: [(methoxy{[3S,3aS,6R,6aS)-6-(nitrooxy) hexahydrofuro[3,2-b]furan-3-yl]oxy}phosphoyryl) oxy]methyl 2-butyl-4-chloro-1-{[2'-(1H-tetrazol-5-yl)biphenyl-4-yl]methyl}-1H-imidazole-5-carboxylate Each diastereomer of [(methoxy{[(3S,3aS,6R,6aS)-6-(nitrooxy)hexahydrofuro[3,2-b]furan-3-yl]oxy}phosphoryl) oxy]methyl 2-butyl-4-chloro-1-{[2'-(1-trityl-1H-tetrazol-5-yl)biphenyl-4-yl]methyl}-1H-imidazole-5-carboxylate was dissolved in methanol and heated to 70° C. for 2 hours. The residue was purified by HPLC reverse phase (C-18), eluting with acetonitrile/water+0.1% trifluoroacetic acid to give the title compound.

D1: $^1$H NMR (500 MHz, CDCl$_3$) δ 7.95 (d, J=7.8 Hz, 1H), 7.59 (t, J=7.3 Hz, 1H), 7.52 (t, J=7.4 Hz, 1H), 7.44 (d, J=7.6 Hz, 1H), 7.12 (d, J=8.0 Hz, 2H), 6.89 8.0 Hz, 2H), 5.72 (dd, J=8.2, 5.9 Hz, 1H), 5.69 (dd, J=9.2, 5.5 Hz, 1H), 5.45 (s, 2H), 5.33 (td, J=5.5, 2.5 Hz, 1H), 4.96 (t, J=5.3 Hz, 1H), 4.80 (dd, J=7.1, 2.5 Hz, 1H), 4.54 (d, J=4.6 Hz, 1H), 4.04 (d, J=11.2 Hz, 1H), 3.96 (dd, J=11.3, 2.4 Hz, 1H), 3.86 (d, J=11.2 Hz, 1H), 3.85 (d, J=11.5 Hz, 1H), 3.74 (d, J=11.4 Hz, 3H), 2.72 (t, J=7.8 Hz, 2H), 1.75 (quintet, J=7.7 Hz, 2H), 1.40 (sextet, J=7.4 Hz, 2H), 0.92 (t, J=7.4 Hz, 3H); LC-MS: m/z 734.3 (M+H).

D2: $^1$H NMR (500 MHz, CDCl$_3$) δ 7.95 (d, J=7.6 Hz, 1H), 7.58 (t, J=7.6 Hz, 1H), 7.52 (t, J=7.4 Hz, 1H), 7.44 (d, J=7.6 Hz, 1H), 7.12 (d, J=8.0 Hz, 2H), 6.89 (d, J=8.0 Hz, 2H), 5.73 (dd, J=9.6, 5.2 Hz, 1H), 5.70 (dd, J=10.3, 5.3 Hz, 1H), 5.45 (s, 2H), 5.30 (td, J=5.5, 2.7 Hz, 1H), 4.90 (t, J=5.2 Hz, 1H), 4.82 (dd, J=7.1, 2.5 Hz, 1H), 4.53 (d, J=4.8 Hz, 1H), 4.02 (d, J=10.9 Hz, 1H), 3.95 (dd, J=11.4, 2.5 Hz, 1H), 3.84 (d, J=112 Hz, 1H), 3.83 (d, J=11.2 Hz, 1H), 3.75 (d, J=11.7 Hz, 3H), 2.72 (t, J=7.8 Hz, 2H), 1.75 (quintet, J=7.7 Hz, 2H), 1.40 (sextet, J=7.5 Hz, 2H), 0.92 (t, J=7.4 Hz, 3H); LC-MS: m/z 734.3 (M+H).

EXAMPLE 14

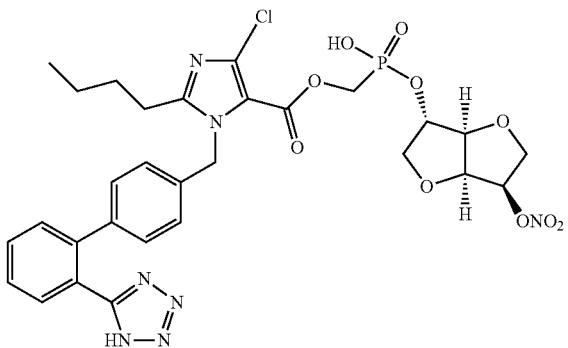

(hydroxy{[(3S,3aS,6R,6aS)-6-(nitrooxy)hexahydrofuro[3,2-b]furan-3-yl]oxy}phosphoryl)methyl 2-butyl-4-chloro-1-{[2'-(1H tetrazol-5-yl)biphenyl-4-yl] methyl}-1H-imidazole-5-carboxylate Step A: (diethoxyphosphoryl)methyl 2-butyl-4-chloro-1-{[2'-(1-trityl-1H-tetrazol-5-yl)biphenyl-4-yl]methyl}-1H-imidazole-5-carboxylate The title compound was prepared by following example 7, except that the reagent 2-butyl-4-chloro-1-{[2'-(1H-tetrazol-5-yl)biphenyl-4-yl]methyl}-1H-imidazole-5-carboxylic acid was replaced by 2-butyl-4-chloro-1-{[2'-(1-trityl-1H-tetrazol-5-yl)biphenyl-4-yl]methyl}-1H-imidazole-5-carboxylic acid, and isosorbide-5-mononitrate was replaced by diethyl (hydroxymethyl)phosphonate. $^1$H NMR (500 MHz, CDCl$_3$) δ 7.94 (d, J=7.4 Hz, 1H), 7.52 (td, J=7.1, 1.3 Hz, 1H), 7.48 (t, J=7.7 Hz, 1H), 7.39-7.34 (m, 4H), 7.28 (t, j=7.8 Hz, 6H), 7.13 (d, J=8.3 Hz, 2H), 6.95 (d, J=8.1 Hz, 6H), 6.80 (d, J=8.1 Hz, 2H), 5.47 (s, 2H), 4.49 (d, J=8.4 Hz, 2H), 4.24-4.16 (m, 4H), 2.53 (t, J=7.8 Hz, 2H), 1.67 (quintet, J=7.7 Hz, 2H), 1.33 (t, J=7.0 Hz, 6H), 1.30 (sextet, J=7.4 Hz, 2H), 0.88 (I, J=7.4 Hz, 3H).

Step B: (diethoxyphosphoryl)methyl 2-butyl-4-chloro-1-{[2'-(1H-tetrazol-5-yl)biphenyl-4-yl]methyl}-1H-imidazole-5-carboxylate The title compound was prepared by following step E in Example 13, except that the reagent [(methoxy{[(3S,3aS,6R,6aS)-6-(nitrooxy)hexahydrofuro[3,2-b]furan-3-yl] oxy}phosphorypoxy]methyl 2-butyl-4-chloro-1-{[2'-(1-trityl-1H-tetrazol-5-yl)biphenyl-4-yl]methyl}-1H-imidazole-5-carboxylate was replaced by (diethoxyphosphoryl)methyl 2-butyl-4-chloro-1-{[2'-(1-trityl-1H-tetrazol-5-yl)biphenyl-4-yl]methyl}-1H-imidazole-5-carboxylate. $^1$H NMR (500 MHz, CDCl$_3$) δ 8.00 (dd, J=7.7, 1.3 Hz, 1H), 7.57 (t, J=7.4 Hz, 1H), 7.50 (td, J=7.6, 1.4 Hz, 1H), 7.44 (d, J=7.8 Hz, 1H), 7.12 (d, J=8.2 Hz, 2H), 6.87 (d, J=8.0 Hz, 2H), 5.45 (s, 2H), 4.48 (d, J=8.9 Hz, 2H), 4.11 (quintet, J=7.3 Hz, 4H), 2.71 (t, J=7.8 Hz, 2H), 1.73 quintet, J=7.7 Hz, 2H), 1.39 (sextet, J=7.4 Hz, 2H), 1.30 (t, J=7.1 Hz, 6H), 0.90 (t, J=7.5 Hz, 3H); LC-MS: m/z 587.1 (M+H).

Step C: ({[(2-butyl-4-chloro-1-{[2'-(1H-tetrazol-5-yl)biphenyl-4-yl]methyl}-1H-imidazol-5-yl)carbonyl]oxy}methyl)phosphonic acid Bromotrimethylsilane (1.70 mL, 13.1 mmol) was added to a stirred, 0° C. mixture of (diethoxyphosphoryl)methyl 2-butyl-4-chloro-1-{[2'-(1H-tetrazol-5-yl)biphenyl-4-yl]methyl}-1H-imidazole-5-carboxylate (3.49 g, 5.95 mmol) in acetonitrile and the mixture was stirred at room temperature for 1 hour. Methanol (20 mL) was added, stirred for 30 minutes then concentrated in vacua to afford the title compound as crude, which was used in the subsequent step without further purification. LC-MS: m/z 531.0 (M+H).

Step D: (hydroxy{[(3S,3aS,6R,6aS)-6-(nitrooxy)hexahydrofuro[3,2-b]furan-3-yl]oxy}phosphoryl) methyl 2-butyl-4-chloro-1-{[2'-(1H-tetrazol-5-yl)biphenyl-4-yl]methyl}-1H-imidazole-5-carboxylate The title compound was prepared by following example 7, except that the reagent 2-butyl-4-chloro-1-{[2'-(1H tetrazol-5-yl)biphenyl-4-yl]methyl}-1H-imidazole-5-carboxylic acid was replaced by ({[(2-butyl-4-chloro-1-{[2'-(1H-tetrazol-5-yl)biphenyl-4-yl]methyl}-1H-imidazol-5-yl)carbonyl] oxy}methyl)phosphonic acid. $^1$H NMR (500 MHz, CDCl$_3$) δ 7.80 (d, J=7.5 Hz, 1H), 7.58 (t, J=7.5 Hz, 1H), 7.47 (t, J=7.5 Hz, 1H), 7.43 (d, J=7.5 Hz, 1H), 7.05 (d, J=7.5 Hz, 2H), 6.88 (d, J=7.5 Hz, 2H), 5.55-5.43 (m, 2H), 5.32-5.25 (m, 4.94-4.87

(m, 1H), 4.87-4.81 (m, 1H), 4.57-4.46 (m, 3H), 3.99-3.86 (m, 2H), 3.86-3.75 (m, 2H), 2.77-2.60 (m, 2H), 1.70-1.60 (m, 2H), 1.38-1.24 (m, 2H), 0.86 (t, J=8.0 Hz, 3H); LC-MS: m/z 704.3 (M+H).

Mononitrate compounds that have been orally dosed to rats result in nitrites (metabolites of nitric oxide) circulating in plasma with maximal concentrations in the 0.5-2 µM range. Similar dosing of isosorbide mononitrate compounds described in this invention results in increased circulating nitrite concentrations. Biochemical evidence for the generation of NO in vivo in response to test compound administration was obtained from studies in Sprague-Dawley rats. Administration of test compound to fasted SD rats (40 mpk, PO) results in the appearance of reactive nitrogen species (RNS), assessed using the diaminonapthalene derivitization (DAN) assay.

RNS were detected as S-nitrosothiols (RNSOs) in EDTA-treated rat plasma using an HPLC fluorescent assay based on the method of Kostka and Park (Methods Enzymol. 1999, 301, 227-235). The method is based on the detection of fluorescent 2,3-naphthotriazole (NAT) formed in the reaction between acidified 2,3-diaminonaphthalene and the nitrosonium moiety of RSNOs released by $HgCl_2$-mediated breakdown of the S—NO bond. The reaction mixture was chromatographed by reversed phase HPLC, and the fluorescent signal of the resolved NAT peak was quantified.

Plasma (20 µL) was first diluted 1:1 in $H_2O$ (20 µL) in a black polypropylene untreated microtiter plate. DAN reagent (100 µL per well, 100 µM DAN in 0.1 N HCl, 4 mM $HgCl_2$) was added, and the plate was immediately sealed with an opaque plate mat, vortexed, and incubated in the dark for 10 min. Plates were centrifuged (2000×g, 5 min) and chilled to 4° C. before HPLC analysis. HPLC was carried out on an Agilent 1200 system using a chilled autosampler (4° C.). Samples were chromatographed on a C8 column (Zorbax Eclipse XDB-C8, 4.6×150 mm, 5 µm) with isocratic elution using a mobile phase of 67% MeOH, 0.1% $NH_4OAc$ and a flow rate of 2 mL/min. NAT fluorescence was monitored at 450 nm using an excitation wavelength of 360 nm. Calibration curves were prepared using $NaNO_2$ in control plasma.

RNS change for Examples 2, 3, 4, 5, 7, 10, 11 and 12 was measured at 1, 3, 6 and 24 hours, and is shown below.

| | DAN ΔRNS (µM) | | | |
|---|---|---|---|---|
| EXAMPLE | 1 h | 3 h | 6 h | 24 h |
| 2 | 2.3 ± 1.0 | 6.1 ± 1.1 | 4.5 ± 1.4 | 1.1 ± 0.7 |
| 3 | 0.5 ± 0.4 | 2.7 ± 0.5 | 3.0 ± 0.5 | 0.1 ± 0.7 |
| 4 | 0.9 ± 0.2 | 2.1 ± 1.4 | 4.2 ± 2.1 | 0.6 ± 0.3 |
| 5 | 0.7 ± 0.5 | 2.5 ± 1.0 | 2.4 ± 1.2 | −0.3 ± 0.6 |
| 7 | 5.4 ± 3.2 | 1.5 ± 1.2 | 0.2 ± 0.3 | −0.3 ± 0.2 |
| 10 | 0.7 ± 0.3 | 2.0 ± 0.4 | 1.9 ± 0.7 | 0.1 ± 0.3 |
| 11 | 1.1 ± 1.2 | 3.3 ± 1.5 | 1.8 ± 2.0 | 0.1 ± 1.8 |
| 12 | 0.5 ± 0.2 | 1.5 ± 0.9 | 1.3 ± 0.6 | 0.0 ± 0.2 |

In vivo measurement of nitric oxide-mediated affects in an oral dog telemetry model indicate that compounds of this invention are superior to corresponding mono- and di-nitrate derivatives.

DATA TABLE 1

| Structure | Compound Number | $EC_{50}$ in vessel relaxation assay |
|---|---|---|
| 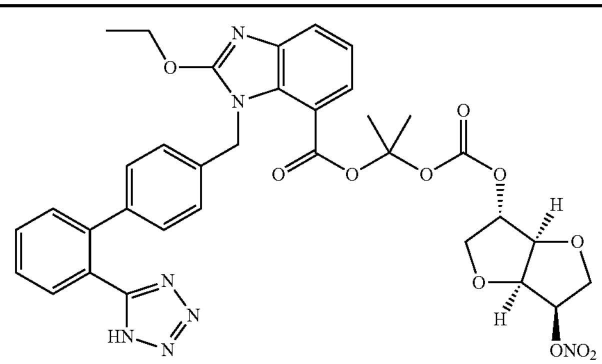 | Example 1 | 14.2 µM |
| 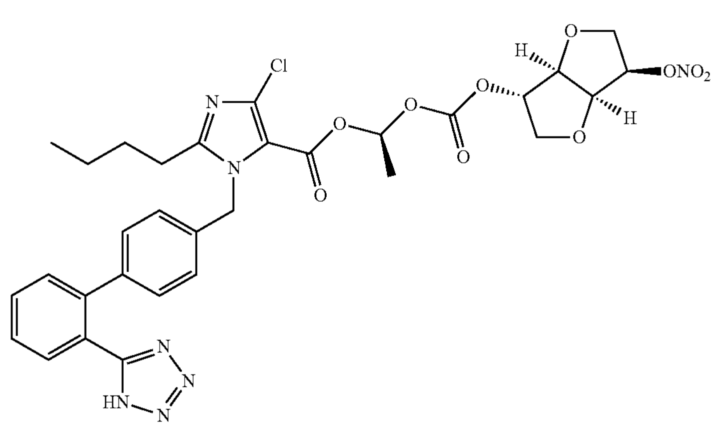 | Example 2 | 9.5 µm |

DATA TABLE 1-continued

| Structure | Compound Number | $EC_{50}$ in vessel relaxation assay |
|---|---|---|
| 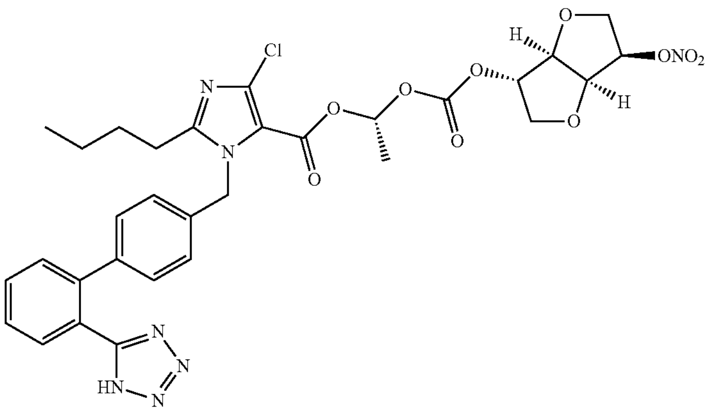 | Example 3 | 15.4 μM |
| 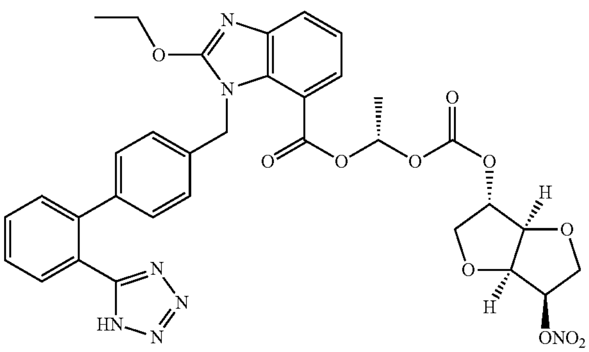 | Example 4 | 8.9 μM |
| 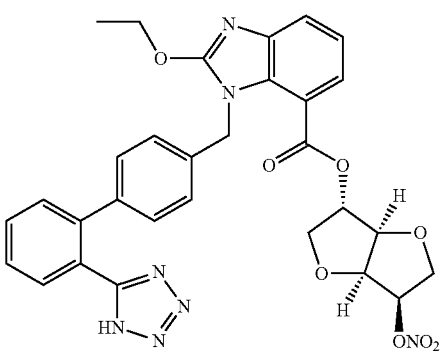 | Example 9 | 5.1 μM |
| 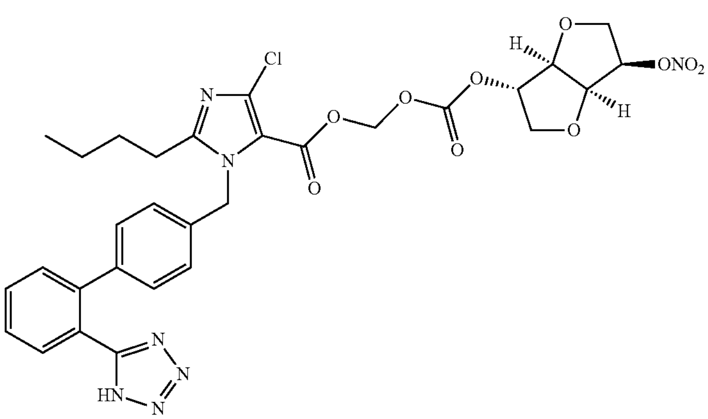 | Example 12 | 20.6 μM |

What is claimed is:

1. A compound having the general formula:

R—Y
|
[Y]₀₋₁ wherein R is

[chemical structure showing imidazole with Cl, butyl chain, biphenyl-tetrazole group, and carboxylate linker]

Y is selected from the group consisting of
1) $R^5$,
2) —C(R¹R²)(C(R³R⁴))₀₋₁ Y¹R⁵, and
3) —C(R¹R²)—O—Y¹R⁵;

R¹, R², R³ and R⁴ are independently selected from the group consisting of hydrogen and $C_{1-4}$ alkyl; and
R⁵ is selected from the group consisting of

[three chemical structures of hexahydrofuro[3,2-b]furan with ONO₂ groups]

Y¹ is selected from the group consisting of —C(O)—O— and —P(O)(OR⁶)—O—; and
R⁶ is hydrogen or CH₃,
or a pharmaceutically acceptable salt thereof.

2. A compound of claim 1, wherein R¹, R², R³ and R⁴ are independently selected from the group consisting of hydrogen and CH₃.

3. A compound of claim 1, wherein Y¹ is selected from the group consisting of —C(O)—O—, —P(O)(OH)—O—, and —P(O)(OCH₃)—O—.

4. A compound of claim 1, wherein Y is selected from the group consisting of
—C((CH₃)(CH₃))OC(O)O—R⁵, —CH(CH₃)OC(O)O—R⁵, —R⁵, —CH₂C(O)O—R⁵, —CH(CH₃)C(O)O—R⁵, —CH₂CH₂C(O)O—R⁵, —CH₂OP(O)(OCH₃)O—R⁵, and —CH₂P(O)(OH)O—R⁵.

5. A compound of claim 4, wherein Y is selected from the group consisting of
—C((CH₃)(CH₃))OC(O)O—R⁵ and —CH(CH₃)OC(O)O—R⁵.

6. A compound of claim 4, wherein Y is selected from the group consisting of —C((CH₃)(CH₃))OC(O)O—R⁵ and —CH(CH₃)OC(O)O—R⁵ wherein R⁵ is

[chemical structure]

7. A compound of claim 4, wherein Y is selected from the group consisting of —C((CH₃)(CH₃))OC(O)O—R⁵ and —CH(CH₃)OC(O)O—R⁵, wherein R⁵ is

[two chemical structures]

8. A compound of claim 1, selected from the group consisting of
(1S)-1-[({[(3S,3aR,6R,6aS)-6-(nitrooxy)hexahydrofuro[3,2-b]furan-3-yl]oxy}carbonyl)oxy]ethyl 2-butyl-4-chloro-1-{[2'-(1H-tetrazol-5-yl)biphenyl-4-yl]methyl}-1H-imidazole-5-carboxylate,
(1R)-1-[({[(3S,3aR,6R,6aS)-6-(nitrooxy)hexahydrofuro[3,2-b]furan-3-yl]oxy}carbonyl)oxy]ethyl 2-butyl-4-chloro-1-{[2'-(1H-tetrazol-5-yl)biphenyl-4-yl]methyl}-1H-imidazole-5-carboxylate,
(3S,3aR,6R,6aS)-6-(nitrooxy)hexahydrofuro[3,2-b]furan-3-yl 2-butyl-4-chloro-1-{[2'-(1H-tetrazol-5-yl)biphenyl-4-yl]methyl}-1H-imidazole-5-carboxylate,
2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate,
(1R)-1-methyl-2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate,
(1S)-1-methyl-2-{[(3S,3aR,6R,6aS)-6-(nitrooxy)hexahydrofuro[3,2-b]furan-3-yl]oxy}-2-oxoethyl 2-butyl-4-chloro-1-{[2'-(1H-tetrazol-5-yl)biphenyl-4-yl]methyl}-1H-imidazole-5-carboxylate,
3-{[(3S,3aR,6R,6aS)-6-(nitrooxy)hexahydrofuro[3,2-b]furan-3-yl]oxy}-3-oxopropyl 2-butyl-4-chloro-1-{[2'-(1H-tetrazol-5-yl)biphenyl-4-yl]methyl}-1H-imidazole-5-carboxylate,
[(methoxy{[(3S,3aS,6R,6aS)-6-(nitrooxy)hexahydrofuro[3,2-b]furan-3-yl]oxy}phosphoryl)oxy]methyl 2-butyl-4-chloro-1-{[2'-(1H-tetrazol-5-yl)biphenyl-4-yl]methyl}-1H-imidazole-5-carboxylate, and
(hydroxy{[(3S,3aS,6R,6aS)-6-(nitrooxy)hexahydrofuro[3,2-b]furan-3-yl]oxy}phosphoryl)methyl 2-butyl-4-chloro-1-{[2'-(1H-tetrazol-5-yl)biphenyl-4-yl]methyl}-1H-imidazole-5-carboxylate, or a pharmaceutically acceptable salt thereof.

9. A pharmaceutical composition comprising a compound of claim 1 and a pharmaceutically acceptable carrier.

10. A pharmaceutical composition comprising a compound of claim 1, a diuretic, and a pharmaceutically acceptable carrier.

11. A method for treating hypertension in a patient which comprises administering to the patient a therapeutically effective amount of the composition of claim 10.

* * * * *